(12) United States Patent
Zhang et al.

(10) Patent No.: US 6,884,905 B2
(45) Date of Patent: Apr. 26, 2005

(54) DEGRADABLE CARBAMATE-CONTAINING BIS(ACRYLOYL) CROSSLINKERS, AND DEGRADABLE CROSSLINKED HYDROGELS COMPRISING THEM

(75) Inventors: Hongmin Zhang, Duxbury, MA (US); Alexander Schwarz, Brookline, MA (US)

(73) Assignee: Biosphere Medical, Rockland, MA (US)

(*) Notice: Subject to any disclaimer, the term of this patent is extended or adjusted under 35 U.S.C. 154(b) by 0 days.

(21) Appl. No.: 10/374,508

(22) Filed: Feb. 25, 2003

(65) Prior Publication Data

US 2004/0024136 A1 Feb. 5, 2004

Related U.S. Application Data

(60) Provisional application No. 60/397,909, filed on Jul. 23, 2002.

(51) Int. Cl.$^7$ .............................................. C07C 271/00
(52) U.S. Cl. ...................................................... 560/158
(58) Field of Search ........................................ 560/158

(56) References Cited

U.S. PATENT DOCUMENTS

| | | | |
|---|---|---|---|
| 3,718,716 A | 2/1973 | Joh et al. ..................... | 260/898 |
| 3,794,494 A | 2/1974 | Kai et al. ..................... | 96/35.1 |
| 3,858,510 A | 1/1975 | Kai et al. ................... | 101/395 |
| 4,637,902 A * | 1/1987 | Hirai et al. .................. | 562/874 |
| 5,124,421 A | 6/1992 | Ulbrich et al. .............. | 526/212 |
| 5,130,479 A | 7/1992 | Ulbrich et al. .............. | 562/874 |
| 5,922,612 A | 7/1999 | Alder et al. ................. | 436/163 |
| 6,323,360 B1 | 11/2001 | Ruckenstein et al. ....... | 560/199 |

FOREIGN PATENT DOCUMENTS

| WO | WO 01/44307 A2 | 6/2001 |
|---|---|---|
| WO | WO 01/68720 A1 | 9/2001 |
| WO | WO 01/68722 A1 | 9/2001 |

OTHER PUBLICATIONS

Argade et al.; "Preparation and Characterization of Novel Biodegradable tri–and tetraacrylate Intermediates", Polymer Bulletin 31: 401–407, (1993).

Bruining et al.; "Biodegradable Three–Dimensional Networks of Poly(dimethylamino ethyl methacrylate). Synthesis, Characterization and in Vitro Studies of Structural Degradation and Cytotoxicity", Biomaterials 21: 595–604, (2000).

Bruining et al.; "New Biodegradable Networks of Poly(N-vinylpyrrolidinone) Designed for controlled Nonburst Degradation in the Vitrreous Body", J Biomed. Mater. Res. 47:189–197, (1999).

Eo, Akala; "Hydrolysis of Linear Copolymers with Pendant N, O–diacylhydroxylamine Moieties)", Pharm. Pharmacol. Lett. 8(3): 129–132, (1998).

Grosse–Sommer and Prud'homme; "Degradable Phosphazene–crosslinked Hydrogels", Journal of Controlled Release 40: 261–267, (1996).

Gombotz and Petit; "Biodegradable Polymers for Protein and Peptide Drug Delivery", Bioconjugate Chem. 6: 332–351,(1995).

Ruckenstein and Zhang; "A Novel Breakable Cross–Linker and pH–Responsive Star–Shaped and Gel Polymers", Macromelecules 32: 3979–3983, (1999).

Sawhney et al.; "Bioerodible Hydrogels Based on Photopolymerized Poly(ethylene glycol)–co–poly(αhydroxy acid) diacrylate Macromers", Macromolecules 26: 581–587, (1993).

Ulbrich et al.; "Synthesis Of Novel Hydrolytically degradable Hydrogels for Controlled Drug Release", Journal of Controlled Release 34: 155–165, (1995).

Ulbrich et al.; "Novel Biodegrdable Hydrogels Prepared Using the divinyl;ic Crosslinking Agent N, O–dimethacryloydroxylamine. 1. Synthesis and Characterization of Rates of Gel Degradation, and Rate of Release of Model Drugs, in Vitro and Vivo", Journal of controlled Release 24: 181–19, (1993).

* cited by examiner

Primary Examiner—Paul A. Zucker
(74) Attorney, Agent, or Firm—Dana M. Gordon; Foley Hoag LLP

(57) ABSTRACT

One aspect of the present invention relates to base-labile, carbamate-containing crosslinkers. A second aspect of the present invention relates to degradable crosslinked polymers and hydrogels comprising a base-labile, carbamate-containing crosslinker. The present invention also relates to methods of preparing base-labile, carbamate-containing crosslinkers. Another aspect of the present invention relates to methods of preparing cross-linked polymers and hydrogels comprising a base-labile, carbamate-containing crosslinker.

18 Claims, No Drawings

DEGRADABLE CARBAMATE-CONTAINING BIS(ACRYLOYL) CROSSLINKERS, AND DEGRADABLE CROSSLINKED HYDROGELS COMPRISING THEM

RELATED APPLICATIONS

This application claims the benefit of the filing date of U.S. Provisional Patent Application Ser. No. 60/397,909, filed Jul. 23, 2002.

BACKGROUND OF THE INVENTION

Biocompatible polymeric materials have been used extensively in medical implant devices. For some applications (e.g., bone fixtures, sutures, drug containing implants etc.), the polymers should be not only biocompatible, but also degradable into non-toxic products. This degradability eliminates the need to remove later the device from the implant site.

The first degradable polymers were based on hydrophobic polymers like PLGA, poly(orthoesters), polyanhydrides and polyiminocarbonates, which degrade hydrolytically into water-soluble monomers and oligomers. The degradation times of these polymers are a function of their chemical composition. The problem with these polymers is the need to keep them completely dry during storage. Additionally, the majority of degradable polymers are essentially hard, brittle materials, developed for drug delivery uses.

Other degradable polymers are based on naturally-occurring polymers, e.g., polysaccharides or polypeptides. The degradation process is based on enzymatic hydrolysis of the polysaccharides or polypeptides. While these products can be formed as hydrogels, and therefore may be stored in an aqueous environment, the degradation time is not controllable due to variable enzyme expression in humans. Additionally, only the unmodified part of the protein or polysaccharide is degradable, while modified sites are not degradable. Furthermore, naturally-derived products have to undergo vigorous testing to ensure that they are free of endotoxins and contaminating proteins. For human- or animal-derived proteins, viral contamination is a constant worry.

Another approach to degradability is to synthesize a hydrogel containing an unstable crosslinker. This approach has been investigated by a number of groups. The first approach was to polymerize the hydrogel in situ using photopolymerization of monomers that contain a hydrolytically labile lactic acid component. The degradation time can be adjusted through the number of lactic acid units incorporated into the monomer. However, prior to polymerization, these monomers must be stored under anhydrous conditions.

Another approach has been to synthesize crosslinkers containing hydrolytically labile carbonate (Bruining et al, Biomaterials 21 (2000) 595–604), ester (Argade et al, Polymer Bulletin 31 (1993) 401–407), or phosphazene linkers (Grosse-Sommer et al, Journal of Controlled Release 40 (1996) 261–267). These hydrogels are not stable under any of the conditions described and begin to degrade immediately following synthesis and exposure to an aqueous environment. Yet another approach utilizes a reduction/oxidation cleavable crosslinker, such as a disulfide bridge. However, the reduction product from the disulfide bridge is two thiols, which are easily reoxidized to the disulfide bridge, thereby restoring the crosslink.

Still another approach would use a crosslinker that is stable under either basic or acidic conditions, and starts to degrade at blood pH, roughly 7.4. Ruckenstein et al (Ruckenstein et al, Macromolecules, 32 (1999) 3979–3983; U.S. Pat. No. 6,323,360) described one such crosslinker as the addition product between ethylene glycol divinyl ether and methacrylic acid. The resulting crosslinker, containing hemiacetal functional groups, is base stable and degrades under acidic conditions. However, the publication does not provide a means to control the degradation time, nor are the described degradation conditions in organic solvents meaningful for biological applications.

Another degradable crosslinker has been described by Ulbrich (Ulbrich et al, Journal of Controlled Release, 24 (1993) 181–190; Ulbrich et al, Journal of Controlled Release, 34 (1995) 155–165; U.S. Pat. No. 5,130,479; U.S. Pat. No. 5,124,421). The crosslinker is N,O-dimethacryloylhydroxylamine. The degradation of this crosslinker is based on the base-catalyzed Lossen rearrangement of substituted hydroxamic acids. The crosslinker appears to be stable under acidic conditions, while degradation occurs at neutral to basic pH. The only way disclosed by Ulbrich et al to control degradation is through the crosslink density. Increasing the crosslink density from 1.2% to 2.4% increases the degradation time from 21 hours to 45 hours at pH 7.4 (U.S. Pat. No. 5,124,421). Akala (Akala, Pharm Pharmacol Lett 8 (1998) 129–132) discovered that the introduction of acrylic acid groups into a linear polymer accelerated the degradation of the pendant N,O-diacylhydroxyamine moieties, an effect not reported by Ulbrich et al.

SUMMARY OF THE INVENTION

In certain embodiments, the present invention relates to a compound represented by 1:

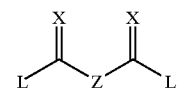

wherein
X represents independently for each occurrence O or S;
L represents independently for each occurrence —O—NH—Q;
Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO(CR$_2$)$_n$C(O)—, 2-alkylacryloylO(CR$_2$)$_n$C(O)—, 3-alkylacryloylO(CR$_2$)$_n$C(O)—, 2,3-dialkylacryloylO(CR$_2$)$_n$C(O)—, 3,3-dialkylacryloylO(CR$_2$)$_n$C(O)—, 2,3,3-trialkylacryloylO(CR$_2$)$_n$C(O)—, (diene)C(O)—, (vinyl)(CR$_2$)$_n$C(O)—, or (vinyl)ArC(O)—;
R represents independently for each occurrence H or alkyl;
Z represents —NH(CR$_2$)$_n$NH—, or —NH(CR$_2$)$_n$J(CR$_2$)$_m$NH—;
Ar represents independently for each occurrence aryl or heteroaryl;
J represents independently for each occurrence O, S, NR, cycloalkyl, heterocyclyl, (CH$_2$CH$_2$O)$_n$, or (CH$_2$CH$_2$N(R))$_n$;
n represents independently for each occurrence an integer in the range 1–10; and
m represents independently for each occurrence an integer in the range 0–10.

In certain embodiments, the present invention relates to a compound represented by 1 and the attendant definitions, wherein X represents O.

In certain embodiments, the present invention relates to a compound represented by 1 and the attendant definitions, wherein L represents —O—NH—Q.

In certain embodiments, the present invention relates to a compound represented by 1 and the attendant definitions, wherein Q represents acryloyl, or 2-methacryloyl.

In certain embodiments, the present invention relates to a compound represented by 1 and the attendant definitions, wherein R represents H.

In certain embodiments, the present invention relates to a compound represented by 1 and the attendant definitions, wherein Z represents —NH(CR$_2$)$_n$NH—.

In certain embodiments, the present invention relates to a compound represented by 1 and the attendant definitions, wherein X represents O; and L represents —O—NH—Q.

In certain embodiments, the present invention relates to a compound represented by 1 and the attendant definitions, wherein X represents O; L represents —O—NH—Q; and Q represents acryloyl, or 2-methacryloyl.

In certain embodiments, the present invention relates to a compound represented by 1 and the attendant definitions, wherein X represents O; L represents —O—NH—Q; Q represents acryloyl, or 2-methacryloyl; and R represents H.

In certain embodiments, the present invention relates to a compound represented by 1 and the attendant definitions, wherein X represents O; L represents —O—NH—Q; Q represents acryloyl, or 2-methacryloyl; R represents H; and Z represents —NH(CR$_2$)$_n$NH—.

In certain embodiments, the present invention relates to a compound represented by 2:

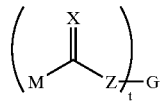

2 wherein
X represents independently for each occurrence O or S;
M represents independently for each occurrence —O—NH—Q;
Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO(CR$_2$)$_n$C(O)—, 2-alkylacryloylO(CR$_2$)$_n$C(O)—, 3-alkylacryloylO(CR$_2$)$_n$C(O)—, 2,3-dialkylacryloylO(CR$_2$)$_n$ C(O)—, 3,3-dialkylacryloylO(CR$_2$)$_n$C(O)—, 2,3,3-trialkylacryloylO(CR$_2$)$_n$C(O)—, (diene)C(O)—, (vinyl)(CR$_2$)$_n$C(O)—, or (vinyl)ArC(O)—;
R represents independently for each occurrence H or alkyl;
Z represents —NH(CR$_2$)$_n$NH—, or —NH(CR$_2$)$_n$J(CR$_2$)$_m$NH—;
Ar represents independently for each occurrence aryl or heteroaryl;
J represents independently for each occurrence O, S, NR, cycloalkyl, heterocyclyl, (CH$_2$CH$_2$O)$_n$, or (CH$_2$CH$_2$N(R))$_n$;
G represents (CR$_{(4-t)}$), aryl, or heteroaryl;
n represents independently for each occurrence an integer in the range 1–10;
m represents independently for each occurrence an integer in the range 0–10; and
t represents 3 or 4.

In certain embodiments, the present invention relates to a compound represented by 2 and the attendant definitions, wherein X represents O.

In certain embodiments, the present invention relates to a compound represented by 2 and the attendant definitions, wherein M represents —O—NH—Q.

In certain embodiments, the present invention relates to a compound represented by 2 and the attendant definitions, wherein Q represents acryloyl, or 2-methacryloyl.

In certain embodiments, the present invention relates to a compound represented by 2 and the attendant definitions, wherein R represents H.

In certain embodiments, the present invention relates to a compound represented by 2 and the attendant definitions, wherein X represents O; and M represents —O—NH—Q.

In certain embodiments, the present invention relates to a compound represented by 2 and the attendant definitions, wherein X represents O; M represents —O—NH—Q; and Q represents acryloyl, or 2-methacryloyl.

In certain embodiments, the present invention relates to a compound represented by 2 and the attendant definitions, wherein X represents O; M represents —O—NH—Q; Q represents acryloyl, or 2-methacryloyl; and R represents H.

In certain embodiments, the present invention relates to a polymer, comprising a monomer represented by 1:

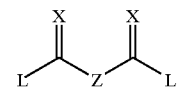

1 wherein
X represents independently for each occurrence O or S;
L represents independently for each occurrence —O—NH—Q;
Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO(CR$_2$)$_n$C(O)—, 2-alkylacryloylO(CR$_2$)$_n$C(O)—, 3-alkylacryloylO(CR$_2$)$_n$C(O)—, 2,3-dialkylacryloylO(CR$_2$)$_n$ C(O)—, 3,3-dialkylacryloylO(CR$_2$)$_n$C(O)—, 2,3,3-trialkylacryloylO(CR$_2$)$_n$C(O)—, (diene)C(O)—, (vinyl)(CR$_2$)$_n$C(O)—, or (vinyl)ArC(O)—;
R represents independently for each occurrence H or alkyl;
Z represents —NH(CR$_2$)$_n$NH—, or —NH(CR$_2$)$_n$J(CR$_2$)$_m$NH—;
Ar represents independently for each occurrence aryl or heteroaryl;
J represents independently for each occurrence O, S, NR, cycloalkyl, heterocyclyl, (CH$_2$CH$_2$O)$_n$, or (CH$_2$CH$_2$N(R))$_n$;
n represents independently for each occurrence an integer in the range 1–10; and
m represents independently for each occurrence an integer in the range 0–10.

In certain embodiments, the present invention relates to a polymer, comprising a monomer represented by 1 and the attendant definitions, wherein X represents O.

In certain embodiments, the present invention relates to a polymer, comprising a monomer represented by 1 and the attendant definitions, wherein L represents —O—NH—Q.

In certain embodiments, the present invention relates to a polymer, comprising a monomer represented by 1 and the attendant definitions, wherein Q represents acryloyl, or 2-methacryloyl.

In certain embodiments, the present invention relates to a polymer, comprising a monomer represented by 1 and the attendant definitions, wherein R represents H.

In certain embodiments, the present invention relates to a polymer, comprising a monomer represented by 1 and the attendant definitions, wherein Z represents —NH(CR$_2$)$_n$NH—.

In certain embodiments, the present invention relates to a polymer, comprising a monomer represented by 1 and the attendant definitions, wherein X represents O; and L represents —O—NH—Q.

In certain embodiments, the present invention relates to a polymer, comprising a monomer represented by 1 and the attendant definitions, wherein X represents O; L represents —O—NH—Q; and Q represents acryloyl, or 2-methacryloyl.

In certain embodiments, the present invention relates to a polymer, comprising a monomer represented by 1 and the attendant definitions, wherein X represents O; L represents —O—NH—Q; Q represents acryloyl, or 2-methacryloyl; and R represents H.

In certain embodiments, the present invention relates to a polymer, comprising a monomer represented by 1 and the attendant definitions, wherein X represents O; L represents —O—NH—Q; Q represents acryloyl, or 2-methacryloyl; R represents H; and Z represents —NH(CR$_2$)$_n$NH—.

In certain embodiments, the present invention relates to a polymer, comprising a monomer represented by 1 and the attendant definitions, further comprising a second monomer selected from the group consisting of acrylic acids, acrylates, and acrylamides.

In certain embodiments, the present invention relates to a polymer, comprising a monomer represented by 1 and the attendant definitions, further comprising a second monomer, wherein said second monomer is acrylic acid, 2-hydroxyethyl acrylate, oligo(ethylene glycol) 2-methacrylate, acrylamide, N,N-dimethylacrylamide, or N-(tris(hyrdoxymethyl)methyl)acrylamide.

In certain embodiments, the present invention relates to a polymer, comprising a monomer represented by 2:

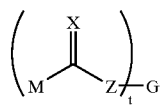

2 wherein
X represents independently for each occurrence O or S;
M represents independently for each occurrence —O—NH—Q;
Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO(CR$_2$)$_n$C(O)—, 2-alkylacryloylO(CR$_2$)$_n$C(O)—, 3-alkylacryloylO(CR$_2$)$_n$C(O)—, 2,3-dialkylacryloylO(CR$_2$)$_n$ C(O)—, 3,3-dialkylacryloylO(CR$_2$)$_n$C(O)—, 2,3,3-trialkylacryloylO(CR$_2$)$_n$C(O)—, (diene)C(O)—, (vinyl)(CR$_2$)$_n$C(O)—, or (vinyl)ArC(O)—;
R represents independently for each occurrence H or alkyl;
Z represents —NH(CR$_2$)$_n$NH—, or —NH(CR$_2$)$_n$J(CR$_2$)$_m$NH—;
Ar represents independently for each occurrence aryl or heteroaryl;
J represents independently for each occurrence O, S, NR, cycloalkyl, heterocyclyl, (CH$_2$CH$_2$O)$_n$, or (CH$_2$CH$_2$N(R))$_n$;
G represents (CR$_{(4-t)}$), aryl, or heteroaryl;
n represents independently for each occurrence an integer in the range 1–10;
m represents independently for each occurrence an integer in the range 0–10; and
t represents 3 or 4.

In certain embodiments, the present invention relates to a polymer, comprising a monomer represented by 2 and the attendant definitions, wherein X represents O.

In certain embodiments, the present invention relates to a polymer, comprising a monomer represented by 2 and the attendant definitions, wherein M represents —O—NH—Q.

In certain embodiments, the present invention relates to a polymer, comprising a monomer represented by 2 and the attendant definitions, wherein Q represents acryloyl, or 2-methacryloyl.

In certain embodiments, the present invention relates to a polymer, comprising a monomer represented by 2 and the attendant definitions, wherein R represents H.

In certain embodiments, the present invention relates to a polymer, comprising a monomer represented by 2 and the attendant definitions, wherein X represents O; and M represents —O—NH—Q.

In certain embodiments, the present invention relates to a polymer, comprising a monomer represented by 2 and the attendant definitions, wherein X represents O; M represents —O—NH—Q; and Q represents acryloyl, or 2-methacryloyl.

In certain embodiments, the present invention relates to a polymer, comprising a monomer represented by 2 and the attendant definitions, wherein X represents O; M represents —O—NH—Q; Q represents acryloyl, or 2-methacryloyl; and R represents H.

In certain embodiments, the present invention relates to a polymer, comprising a monomer represented by 2 and the attendant definitions, further comprising a second monomer selected from the group consisting of acrylic acids, acrylates, and acrylamides.

In certain embodiments, the present invention relates to a polymer, comprising a monomer represented by 2 and the attendant definitions, further comprising a second monomer, wherein said second monomer is acrylic acid, 2-hydroxyethyl acrylate, oligo(ethylene glycol) 2-methacrylate, acrylamide, N,N-dimethylacrylamide, or N-(tris(hyrdoxymethyl)methyl)acrylamide.

In certain embodiments, the present invention relates to a crosslinked gel, comprising a hydrophobic polymer; and a crosslinker selected from the group consisting of a compound represented by 1 or 2 and one of the sets of attendant definitions.

In certain embodiments, the present invention relates to a crosslinked gel, comprising a hydrophobic polymer; and a crosslinker selected from the group consisting of a compound represented by 1 or 2 and one of the sets of attendant definitions, wherein said hydrophobic polymer comprises an alkyl acrylate, alkyl alkylacrylate, alkyl acrylamide, or alkyl alkylacrylamide.

In certain embodiments, the present invention relates to a crosslinked gel, comprising a hydrophobic polymer; and a crosslinker selected from the group consisting of a compound represented by 1 or 2 and one of the sets of attendant definitions, wherein said hydrophobic polymer comprises an alkyl methacrylate.

In certain embodiments, the present invention relates to a crosslinked gel, comprising a hydrophobic polymer; and a crosslinker selected from the group consisting of a compound represented by 1 or 2 and one of the sets of attendant definitions, wherein said hydrophobic polymer comprises methyl methacrylate, ethyl methacrylate, n-butyl methacrylate, or tert-butyl methacrylate.

In certain embodiments, the present invention relates to a crosslinked hydrogel, comprising a hydrophilic polymer; and a crosslinker selected from the group consisting of a compound represented by 1 or 2 and one of the sets of attendant definitions.

In certain embodiments, the present invention relates to a crosslinked hydrogel, comprising a hydrophilic polymer;

and a crosslinker selected from the group consisting of a compound represented by 1 or 2 and one of the sets of attendant definitions, wherein said hydrophilic polymer comprises an acrylic acid, acrylate, or acrylamide.

In certain embodiments, the present invention relates to a crosslinked hydrogel, comprising a hydrophilic polymer; and a crosslinker selected from the group consisting of a compound represented by 1 or 2 and one of the sets of attendant definitions, wherein said hydrophilic polymer comprises acrylic acid, 2-hydroxyethyl acrylate, oligo (ethylene glycol) 2-methacrylate, acrylamide, N,N-dimethylacrylamide, or N-(tris(hydroxymethyl)methyl) acrylamide.

In certain embodiments, the present invention relates to a crosslinked hydrogel, comprising a hydrophilic polymer; and a crosslinker selected from the group consisting of a compound represented by 1 or 2 and one of the sets of attendant definitions, wherein said hydrophilic polymer consists of a first acrylamide and a second acrylamide.

In certain embodiments, the present invention relates to a crosslinked hydrogel, comprising a hydrophilic polymer; and a crosslinker selected from the group consisting of a compound represented by 1 or 2 and one of the sets of attendant definitions, wherein said hydrophilic polymer consists of a first acrylamide and a second acrylamide, wherein said first acrylamide is acrylamide or N,N-dimethylacrylamide.

In certain embodiments, the present invention relates to a crosslinked hydrogel, comprising a hydrophilic polymer; and a crosslinker selected from the group consisting of a compound represented by 1 or 2 and one of the sets of attendant definitions, wherein said hydrophilic polymer consists of a first acrylamide and a second acrylamide, wherein said second acrylamide is N-(tris(hydroxymethyl)methyl) acrylamide.

In certain embodiments, the present invention relates to a crosslinked hydrogel, comprising a hydrophilic polymer; and a crosslinker selected from the group consisting of a compound represented by 1 or 2 and one of the sets of attendant definitions, wherein said hydrophilic polymer consists of a first acrylamide and a second acrylamide, wherein said first acrylamide is acrylamide or N,N-dimethylacrylamide; and said second acrylamide is N-(tris (hydroxymethyl)methyl)acrylamide.

In certain embodiments, the present invention relates to a crosslinked hydrogel, comprising a hydrophilic polymer; and a crosslinker selected from the group consisting of a compound represented by 1 or 2 and one of the sets of attendant definitions, wherein said hydrophilic polymer consists of an acrylamide and an acrylate.

In certain embodiments, the present invention relates to a crosslinked hydrogel, comprising a hydrophilic polymer; and a crosslinker selected from the group consisting of a compound represented by 1 or 2 and one of the sets of attendant definitions, wherein said hydrophilic polymer consists of an acrylamide and an acrylate, wherein said acrylamide is acrylamide or N,N-dimethylacrylamide.

In certain embodiments, the present invention relates to a crosslinked hydrogel, comprising a hydrophilic polymer; and a crosslinker selected from the group consisting of a compound represented by 1 or 2 and one of the sets of attendant definitions, wherein said hydrophilic polymer consists of an acrylamide and an acrylate, wherein said acrylate is acrylic acid, 2-hydroxyethyl acrylate, or oligo(ethylene glycol) 2-methacrylate.

In certain embodiments, the present invention relates to a crosslinked hydrogel, comprising a hydrophilic polymer; and a crosslinker selected from the group consisting of a compound represented by 1 or 2 and one of the sets of attendant definitions, wherein said hydrophilic polymer consists of an acrylamide and an acrylate, wherein said acrylamide is acrylamide or N,N-dimethylacrylamide; and said acrylate is acrylic acid, 2-hydroxyethyl acrylate, or oligo (ethylene glycol) 2-methacrylate.

In certain embodiments, the present invention relates to a crosslinked hydrogel, comprising a hydrophilic polymer; and a crosslinker selected from the group consisting of a compound represented by 1 or 2 and one of the sets of attendant definitions, wherein said hydrophilic polymer consists of a first acrylate and a second acrylate.

In certain embodiments, the present invention relates to a crosslinked hydrogel, comprising a hydrophilic polymer; and a crosslinker selected from the group consisting of a compound represented by 1 or 2 and one of the sets of attendant definitions, wherein said hydrophilic polymer consists of a first acrylate and a second acrylate, wherein said first acrylate is acrylic acid, 2-hydroxyethyl acrylate, or oligo(ethylene glycol) 2-methacrylate.

In certain embodiments, the present invention relates to a crosslinked hydrogel, comprising a hydrophilic polymer; and a crosslinker selected from the group consisting of a compound represented by 1 or 2 and one of the sets of attendant definitions, wherein said hydrophilic polymer consists of a first acrylate and a second acrylate, wherein said first acrylate is acrylic acid, 2-hydroxyethyl acrylate, or oligo(ethylene glycol) 2-methacrylate; and said second acrylate is acrylic acid, 2-hydroxyethyl acrylate, or oligo (ethylene glycol) 2-methacrylate.

In certain embodiments, the present invention relates to a method of preparing a compound represented by 1:

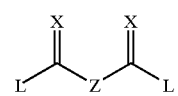

1 wherein
X represents independently for each occurrence O or S;
L represents independently for each occurrence —O—NH—Q;
Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO(CR$_2$)$_n$C(O)—, 2-alkylacryloylO(CR$_2$)$_n$C(O)—, 3-alkylacryloylO(CR$_2$)$_n$C(O)—, 2,3-dialkylacryloylO(CR$_2$)$_n$C(O)—, 3,3-dialkylacryloylO(CR$_2$)$_n$C(O)—, 2,3,3-trialkylacryloylO(CR$_2$)$_n$C(O)—, (diene)C(O)—, (vinyl)(CR$_2$)$_n$C(O)—, or (vinyl)ArC(O)—;
R represents independently for each occurrence H or alkyl;
Z represents —NH(CR$_2$)$_n$NH—, or —NH(CR$_2$)$_n$J(CR$_2$)$_m$NH—;
Ar represents independently for each occurrence aryl or heteroaryl;
J represents independently for each occurrence O, S, NR, cycloalkyl, heterocyclyl, (CH$_2$CH$_2$O)$_n$, or (CH$_2$CH$_2$N(R))$_n$;
n represents independently for each occurrence an integer in the range 1–10; and
m represents independently for each occurrence an integer in the range 0–10;
comprising:
(a) reacting a hydroxylamine with an acrylate, thereby forming an acrylic hydroxamic acid; and
(b) reacting said acrylic hydroxamic acid with a diisocyanate.

In certain embodiments, the present invention relates to a method of preparing a compound represented by 2:

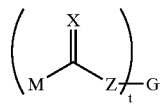

wherein
X represents independently for each occurrence O or S;
M represents independently for each occurrence —O—NH—Q;
Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO(CR$_2$)$_n$C(O)—, 2-alkylacryloylO(CR$_2$)$_n$C(O)—, 3-alkylacryloylO(CR$_2$)$_n$C(O)—, 2,3-dialkylacryloylO(CR$_2$)$_n$C(O)—, 3,3-dialkylacryloylO(CR$_2$)$_n$C(O)—, 2,3,3-trialkylacryloylO(CR$_2$)$_n$C(O)—, (diene)C(O)—, (vinyl)(CR$_2$)$_n$C(O)—, or (vinyl)ArC(O)—;
R represents independently for each occurrence H or alkyl;
Z represents —NH(CR$_2$)$_n$NH—, or —NH(CR$_2$)$_n$J(CR$_2$)$_m$NH—;
Ar represents independently for each occurrence aryl or heteroaryl;
J represents independently for each occurrence O, S, NR, cycloalkyl, heterocyclyl, (CH$_2$CH$_2$O)$_n$, or (CH$_2$CH$_2$N(R))$_n$;
G represents (CR$_{(4-t)}$), aryl, or heteroaryl;
n represents independently for each occurrence an integer in the range 1–10;
m represents independently for each occurrence an integer in the range 0–10; and
t represents 3 or 4;
comprising:
(a) reacting a hydroxylamine with an acrylate, thereby forming a hydroxamic acid; and
(b) reacting said hydroxamic acid with a triisocyanate or tetraisocyanate.

In certain embodiments, the present invention relates to a method of preparing a polymer comprising a monomer represented by 1:

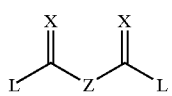

wherein
X represents independently for each occurrence O or S;
L represents independently for each occurrence —O—NH—Q;
Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO(CR$_2$)$_n$C(O)—, 2-alkylacryloylO(CR$_2$)$_n$C(O)—, 3-alkylacryloylO(CR$_2$)$_n$C(O)—, 2,3-dialkylacryloylO(CR$_2$)$_n$C(O)—, 3,3-dialkylacryloylO(CR$_2$)$_n$C(O)—, 2,3,3-trialkylacryloylO(CR$_2$)$_n$C(O)—, (diene)C(O)—, (vinyl)(CR$_2$)$_n$C(O)—, or (vinyl)ArC(O)—;
R represents independently for each occurrence H or alkyl;
Z represents —NH(CR$_2$)$_n$NH—, or —NH(CR$_2$)$_n$J(CR$_2$)$_m$NH—;
Ar represents independently for each occurrence aryl or heteroaryl;
J represents independently for each occurrence O, S, NR, cycloalkyl, heterocyclyl, (CH$_2$CH$_2$O)$_n$, or (CH$_2$CH$_2$N(R))$_n$;
n represents independently for each occurrence an integer in the range 1–10; and
m represents independently for each occurrence an integer in the range 0–10;
comprising:
a) reacting a monomer represented by 1 with a second monomer in the presence of an initiator.

In certain embodiments, the present invention relates to a method of preparing a polymer comprising a monomer represented by 2:

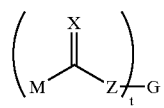

wherein
X represents independently for each occurrence O or S;
M represents independently for each occurrence —O—NH—Q;
Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO(CR$_2$)$_n$C(O)—, 2-alkylacryloylO(CR$_2$)$_n$C(O)—, 3-alkylacryloylO(CR$_2$)$_n$C(O)—, 2,3-dialkylacryloylO(CR$_2$)$_n$C(O)—, 3,3-dialkylacryloylO(CR$_2$)$_n$C(O)—, 2,3,3-trialkylacryloylO(CR$_2$)$_n$C(O)—, (diene)C(O)—, (vinyl)(CR$_2$)$_n$C(O)—, or (vinyl)ArC(O)—;
R represents independently for each occurrence H or alkyl;
Z represents —NH(CR$_2$)$_n$NH—, or —NH(CR$_2$)$_n$J(CR$_2$)$_m$NH—;
Ar represents independently for each occurrence aryl or heteroaryl;
J represents independently for each occurrence O, S, NR, cycloalkyl, heterocyclyl, (CH$_2$CH$_2$O)$_n$, or (CH$_2$CH$_2$N(R))$_n$;
G represents (CR$_{(4-t)}$), aryl, or heteroaryl;
n represents independently for each occurrence an integer in the range 1–10;
m represents independently for each occurrence an integer in the range 0–10; and
t represents 3 or 4;
comprising:
a) reacting a monomer represented by 2 with a second monomer in the presence of an initiator.

In certain embodiments, the present invention relates to a method of preparing a crosslinked gel, comprising a hydrophobic polymer, and a crosslinker represented by 1:

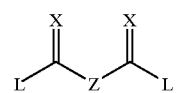

wherein
X represents independently for each occurrence O or S;
L represents independently for each occurrence —O—NH—Q;
Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO(CR$_2$)$_n$C(O)—, 2-alkylacryloylO(CR$_2$)$_n$C(O)—, 3-alkylacryloylO(CR$_2$)$_n$C(O)—, 2,3-dialkylacryloylO(CR$_2$)$_n$C(O)—, 3,3-dialkylacryloylO(CR$_2$)$_n$C(O)—, 2,3,3-trialkylacryloylO $(CR_2)_nC(O)$—, (diene)C(O)—, (vinyl)$(CR_2)_nC(O)$—, or (vinyl)ArC(O)—;

R represents independently for each occurrence H or alkyl;

Z represents —NH$(CR_2)_n$NH—, or —NH$(CR_2)_n$J$(CR_2)_m$—;

Ar represents independently for each occurrence aryl or heteroaryl;

J represents independently for each occurrence O, S, NR, cycloalkyl, heterocyclyl, $(CH_2CH_2O)_n$, or $(CH_2CH_2N(R))_n$;

n represents independently for each occurrence an integer in the range 1–10; and m represents independently for each occurrence an integer in the range 0–10;

comprising:

a) reacting a monomer represented by 1 with a hydrophobic monomer in the presence of an initiator.

In certain embodiments, the present invention relates to a method of preparing a crosslinked gel comprising a hydrophobic polymer and a crosslinker represented by 2:

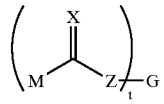

2 wherein

X represents independently for each occurrence O or S;

M represents independently for each occurrence —O—NH—Q;

Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO$(CR_2)_nC(O)$—, 2-alkylacryloylO$(CR_2)_nC(O)$—, 3-alkylacryloylO$(CR_2)_nC(O)$—, 2,3-dialkylacryloylO$(CR_2)_n$—, 3,3-dialkylacryloylO$(CR_2)_nC(O)$—, 2,3,3-trialkylacryloylO$(CR_2)_nC(O)$—, (diene)C(O)—, (vinyl)$(CR_2)_nC(O)$—, or (vinyl)ArC(O)—;

R represents independently for each occurrence H or alkyl;

Z represents —NH$(CR_2)_n$NH—, or —NH$(CR_2)_n$J$(CR_2)_m$NH—;

Ar represents independently for each occurrence aryl or heteroaryl;

J represents independently for each occurrence O, S, NR, cycloalkyl, heterocyclyl, $(CH_2CH_2O)_n$, or $(CH_2CH_2N(R))_n$;

G represents $(CR_{(4-t)})$, aryl, or heteroaryl;

n represents independently for each occurrence an integer in the range 1–10;

m represents independently for each occurrence an integer in the range 0–10; and t represents 3 or 4;

comprising:

a) reacting a monomer represented by 2 with a hydrophobic monomer in the presence of an initiator.

In certain embodiments, the present invention relates to a method of preparing a crosslinked hydrogel, comprising a hydrophilic polymer and a crosslinker represented by 1:

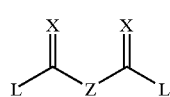

1 wherein

X represents independently for each occurrence O or S;

L represents independently for each occurrence —O—NH—Q;

Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO$(CR_2)_nC(O)$—, 2-alkylacryloylO$(CR_2)_nC(O)$—, 3-alkylacryloylO$(CR_2)_nC(O)$—, 2,3-dialkylacryloylO$(CR_2)_nC(O)$—, 3,3-dialkylacryloylO$(CR_2)_nC(O)$—, 2,3,3-trialkylacryloylO$(CR_2)_nC(O)$—, (diene)C(O)—, (vinyl)$(CR_2)_nC(O)$—, or (vinyl)ArC(O)—;

R represents independently for each occurrence H or alkyl;

Z represents —NH$(CR_2)_n$NH—, or —NH$(CR_2)_n$J$(CR_2)_m$NH—;

Ar represents independently for each occurrence aryl or heteroaryl;

J represents independently for each occurrence O, S, NR, cycloalkyl, heterocyclyl, $(CH_2CH_2O)_n$, or $(CH_2CH_2N(R))_n$;

n represents independently for each occurrence an integer in the range 1–10; and m represents independently for each occurrence an integer in the range 0–10;

comprising:

a) reacting a monomer represented by 1 with a hydrophilic monomer in the presence of an initiator.

In certain embodiments, the present invention relates to a method of preparing a crosslinked hydrogel, comprising a hydrophilic polymer and a crosslinker represented by 2:

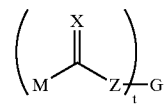

2 wherein

X represents independently for each occurrence O or S;

M represents independently for each occurrence —O—NH—Q;

Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO$(CR_2)_nC(O)$—, 2-alkylacryloylO$(CR_2)_nC(O)$—, 3-alkylacryloylO$(CR_2)_nC(O)$—, 2,3-dialkylacryloylO$(CR_2)_nC(O)$—, 3,3-dialkylacryloylO$(CR_2)_nC(O)$—, 2,3,3-trialkylacryloylO$(CR_2)_nC(O)$—, (diene)C(O)—, (vinyl)$(CR_2)_nC(O)$—, or (vinyl)ArC(O)—;

R represents independently for each occurrence H or alkyl;

Z represents —NH$(CR_2)_n$NH—, or —NH$(CR_2)_n$J$(CR_2)_m$NH—;

Ar represents independently for each occurrence aryl or heteroaryl;

J represents independently for each occurrence O, S, NR, cycloalkyl, heterocyclyl, $(CH_2CH_2O)_n$, or $(CH_2CH_2N(R))_n$;

G represents $(CR_{(4-t)})$, aryl, or heteroaryl;

n represents independently for each occurrence an integer in the range 1–10;

m represents independently for each occurrence an integer in the range 0–10; and t represents 3 or 4;

comprising:

a) reacting a monomer represented by 1 with a hydrophilic monomer in the presence of an initiator.

DETAILED DESCRIPTION OF THE INVENTION

One aspect of the present invention relates to base-labile, carbamate-containing crosslinkers. A second aspect of the present invention relates to degradable crosslinked polymers and hydrogels comprising a base-labile, carbamate-containing crosslinker. The present invention also relates to methods of preparing base-labile, carbamate-containing crosslinkers. Another aspect of the present invention relates to methods of preparing cross-linked polymers and hydrogels comprising a base-labile, carbamate-containing crosslinker.

Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

The term "crosslinking agent", as used herein, refers to any chemical agent that joins distinct chains of a polymer through covalent bonds.

The term "initiator", as used herein, refers to any compound which initiates polymerization, or produces a reactive species which initiates polymerization.

The term "polymer", as used herein, refers to a natural or synthetic compound of unusually high molecular weight consisting of a repeating monomeric unit.

The term "polymerization", as used herein, refers to the bonding of two or more monomers to form a polymer.

The term "monomer", as used herein, refers to a molecule that can combine with another to form a polymer; it is the repeating unit of a polymer.

The term "biocompatible", as used herein, refers to having the property of being biologically compatible by not producing a toxic, injurious, or immunological response in living tissue.

The term "degradable", as used herein, refers to having the property of breaking down or degrading under certain conditions, e.g., at neutral or basic pH.

The term "hydrogel", as used herein refers to a type of gel in which the disperse phase has combined with water to produce a semisolid material.

The term "heteroatom" as used herein means an atom of any element other than carbon or hydrogen. Preferred heteroatoms are boron, nitrogen, oxygen, phosphorus, sulfur and selenium.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, azetidine, azepine, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The terms "amine" and "amino" are art-recognized and refer to both unsubstituted and substituted amines, e.g., a moiety that can be represented by the general formula:

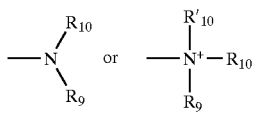

wherein R$_9$, R$_{10}$ and R'$_{10}$ each independently represent a group permitted by the rules of valence.

The term "acylamino" is art-recognized and refers to a moiety that can be represented by the general formula:

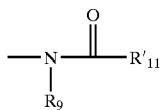

wherein R$_9$ is as defined above, and R'$_{11}$ represents a hydrogen, an alkyl, an alkenyl or —(CH$_2$)$_m$—R$_8$, where m and R$_8$ are as defined above.

The term "amido" is art recognized as an amino-substituted carbonyl and includes a moiety that can be represented by the general formula:

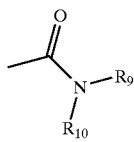

wherein R$_9$, R$_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$_8$, wherein m and R$_8$ are defined above. Representative alkylthio groups include methylthio, ethyl thio, and the like.

The term "carbonyl" is art recognized and includes such moieties as can be represented by the general formula:

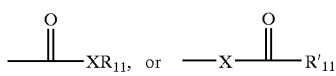

wherein X is a bond or represents an oxygen or a sulfur, and R$_{11}$ represents a hydrogen, an alkyl, an alkenyl, —(CH$_2$)$_m$—R$_8$ or a pharmaceutically acceptable salt, R'$_{11}$ represents a hydrogen, an alkyl, an alkenyl or —(CH$_2$)$_m$—R$_8$, where m and R$_8$ are as defined above. Where X is an oxygen and R$_{11}$ or R'$^{11}$ is not hydrogen, the formula represents an "ester". Where X is an oxygen, and R$_{11}$ is as defined above, the moiety is referred to herein as a carboxyl group, and particularly when R$_{11}$ is a hydrogen, the formula represents a "carboxylic acid". Where X is an oxygen, and R'$_{11}$ is hydrogen, the formula represents a "formate". In general, where the oxygen atom of the above formula is replaced by sulfur, the formula represents a "thiolcarbonyl" group.

Where X is a sulfur and R$_{11}$ or R'$_{11}$ is not hydrogen, the formula represents a "thiolester." Where X is a sulfur and R$_{11}$ is hydrogen, the formula represents a "thiolcarboxylic acid." Where X is a sulfur and R$_{11}$' is hydrogen, the formula represents a "thiolformate." On the other hand, where X is a bond, and R$_{11}$ is not hydrogen, the above formula represents a "ketone" group. Where X is a bond, and R$_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—(CH$_2$)$_m$—R$_8$, where m and R$_8$ are described above.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.;

Wuts, P. G. M. *Protective Groups in Organic Synthesis*, 2$^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, it may be isolated using chiral chromatography methods, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to opioid receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986–87, inside cover.

Compounds of the Invention

In certain embodiments, the present invention relates to a compound represented by 1:

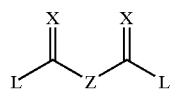

1 wherein

X represents independently for each occurrence O or S;

L represents independently for each occurrence —O—NH—Q;

Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO(CR$_2$)$_n$C(O)—, 2-alkylacryloylO(CR$_2$)$_n$C(O)—, 3-alkylacryloylO(CR$_2$)$_n$C(O)—, 2,3-dialkylacryloylO(CR$_2$)$_n$C(O)—, 3,3-dialkylacryloylO(CR$_2$)$_n$C(O)—, 2,3,3-trialkylacryloylO(CR$_2$)$_n$C(O)—, (diene)C(O)—, (vinyl)(CR$_2$)$_n$C(O)—, or (vinyl)ArC(O)—;

R represents independently for each occurrence H or alkyl;

Z represents —NH(CR$_2$)$_n$NH—, or —NH(CR$_2$)$_n$J(CR$_2$)$_m$NH—;

Ar represents independently for each occurrence aryl or heteroaryl;

J represents independently for each occurrence O, S, NR, cycloalkyl, heterocyclyl, (CH$_2$CH$_2$O)$_n$, or (CH$_2$CH$_2$N(R))$_n$;

n represents independently for each occurrence an integer in the range 1–10; and m represents independently for each occurrence an integer in the range 0–10.

In certain embodiments, the present invention relates to a compound represented by 1 and the attendant definitions, wherein X represents O.

In certain embodiments, the present invention relates to a compound represented by 1 and the attendant definitions, wherein L represents —O—NH—Q.

In certain embodiments, the present invention relates to a compound represented by 1 and the attendant definitions, wherein Q represents acryloyl, or 2-methacryloyl.

In certain embodiments, the present invention relates to a compound represented by 1 and the attendant definitions, wherein R represents H.

In certain embodiments, the present invention relates to a compound represented by 1 and the attendant definitions, wherein Z represents —NH(CR$_2$)$_n$NH—.

In certain embodiments, the present invention relates to a compound represented by 1 and the attendant definitions, wherein X represents O; and L represents —O—NH—Q.

In certain embodiments, the present invention relates to a compound represented by 1 and the attendant definitions, wherein X represents O; L represents —O—NH—Q; and Q represents acryloyl, or 2-methacryloyl.

In certain embodiments, the present invention relates to a compound represented by 1 and the attendant definitions, wherein X represents O; L represents —O—NH—Q; Q represents acryloyl, or 2-methacryloyl; and R represents H.

In certain embodiments, the present invention relates to a compound represented by 1 and the attendant definitions, wherein X represents O; L represents —O—NH—Q; Q represents acryloyl, or 2-methacryloyl; R represents H; and Z represents —NH(CR$_2$)$_n$NH—.

In certain embodiments, the present invention relates to a method of preparing a compound represented by 1 and the attendant definitions, comprising reacting a hydroxylamine with an acrylate, thereby forming an acrylic hydroxamic acid; and reacting said acrylic hydroxamic acid with a diisocyanate.

In certain embodiments, the present invention relates to a compound represented by 2:

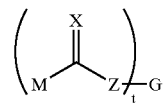

2 wherein

X represents independently for each occurrence O or S;

M represents independently for each occurrence —O—NH—Q;

Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO(CR$_2$)$_n$C(O)—, 2-alkylacryloylO(CR$_2$)$_n$C(O)—, 3-alkylacryloylO(CR$_2$)$_n$C(O)—, 2,3-dialkylacryloylO(CR$_2$)$_n$C(O)—, 3,3- dialkylacryloylO(CR$_2$)$_n$C(O)—, 2,3,3-trialkylacryloylO(CR$_2$)$_n$C(O)—, (diene)C(O)—, (vinyl)(CR$_2$)$_n$C(O)—, or (vinyl)ArC(O)—;

R represents independently for each occurrence H or alkyl;

Z represents —NH(CR$_2$)$_n$NH—, or —NH(CR$_2$)$_n$J(CR$_2$)$_m$NH—;

Ar represents independently for each occurrence aryl or heteroaryl;

J represents independently for each occurrence O, S, NR, cycloalkyl, heterocyclyl, (CH$_2$CH$_2$O)$_n$, or (CH$_2$CH$_2$N(R))$_n$;

G represents (CR$_{(4-t)}$), aryl, or heteroaryl;

n represents independently for each occurrence an integer in the range 1–10;

m represents independently for each occurrence an integer in the range 0–10; and t represents 3 or 4.

In certain embodiments, the present invention relates to a compound represented by 2 and the attendant definitions, wherein X represents O.

In certain embodiments, the present invention relates to a compound represented by 2 and the attendant definitions, wherein M represents —O—NH—Q.

In certain embodiments, the present invention relates to a compound represented by 2 and the attendant definitions, wherein Q represents acryloyl, or 2-methacryloyl.

In certain embodiments, the present invention relates to a compound represented by 2 and the attendant definitions, wherein R represents H.

In certain embodiments, the present invention relates to a compound represented by 2 and the attendant definitions, wherein X represents O; and M represents —O—NH—Q.

In certain embodiments, the present invention relates to a compound represented by 2 and the attendant definitions, wherein X represents O; M represents —O—NH—Q; and Q represents acryloyl, or 2-methacryloyl.

In certain embodiments, the present invention relates to a compound represented by 2 and the attendant definitions, wherein X represents O; M represents —O—NH—Q; Q represents acryloyl, or 2-methacryloyl; and R represents H.

In certain embodiments, the present invention relates to a method of preparing a compound represented by 2 and the attendant definitions, comprising reacting a hydroxylamine with an acrylate, thereby forming a hydroxamic acid; and reacting said hydroxamic acid with a triisocyanate or tetraisocyanate.

Polymers of the Invention

In certain embodiments, the present invention relates to a polymer, comprising a monomer represented by 1:

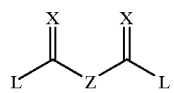

1 wherein

X represents independently for each occurrence O or S;

L represents independently for each occurrence —O—NH—Q;

Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO(CR$_2$)$_n$C(O)—, 2-alkylacryloylO(CR$_2$)$_n$C(O)—, 3-alkylacryloylO(CR$_2$)$_n$C(O)—, 2,3-dialkylacryloylO(CR$_2$)$_n$C(O)—, 3,3-dialkylacryloylO(CR$_2$)$_n$C(O)—, 2,3,3-trialkylacryloylO(CR$_2$)$_n$C(O)—, (diene)C(O)—, (vinyl)(CR$_2$)$_n$C(O)—, or (vinyl)ArC(O)—;

R represents independently for each occurrence H or alkyl;

Z represents —NH(CR$_2$)$_n$NH—, or —NH(CR$_2$)$_n$J(CR$_2$)$_m$NH—;

Ar represents independently for each occurrence aryl or heteroaryl;

J represents independently for each occurrence O, S, NR, cycloalkyl, heterocyclyl, (CH$_2$CH$_2$O)$_n$, or (CH$_2$CH$_2$N(R))$_n$;

n represents independently for each occurrence an integer in the range 1–10; and m represents independently for each occurrence an integer in the range 0–10.

In certain embodiments, the present invention relates to a polymer, comprising a monomer represented by 1 and the attendant definitions, wherein X represents O.

In certain embodiments, the present invention relates to a polymer, comprising a monomer represented by 1 and the attendant definitions, wherein L represents —O—NH—Q.

In certain embodiments, the present invention relates to a polymer, comprising a monomer represented by 1 and the attendant definitions, wherein Q represents acryloyl, or 2-methacryloyl.

In certain embodiments, the present invention relates to a polymer, comprising a monomer represented by 1 and the attendant definitions, wherein R represents H.

In certain embodiments, the present invention relates to a polymer, comprising a monomer represented by 1 and the attendant definitions, wherein Z represents —NH(CR$_2$)$_n$NH—.

In certain embodiments, the present invention relates to a polymer, comprising a monomer represented by 1 and the attendant definitions, wherein X represents O; and L represents —O—NH—Q.

In certain embodiments, the present invention relates to a polymer, comprising a monomer represented by 1 and the attendant definitions, wherein X represents O; L represents —O—NH—Q; and Q represents acryloyl, or 2-methacryloyl.

In certain embodiments, the present invention relates to a polymer, comprising a monomer represented by 1 and the attendant definitions, wherein X represents O; L represents —O—NH—Q; Q represents acryloyl, or 2-methacryloyl; and R represents H.

In certain embodiments, the present invention relates to a polymer, comprising a monomer represented by 1 and the attendant definitions, wherein X represents O; L represents —O—NH—Q; Q represents acryloyl, or 2-methacryloyl; R represents H; and Z represents —NH(CR$_2$)$_n$NH—.

In certain embodiments, the present invention relates to a polymer, comprising a monomer represented by 1 and the attendant definitions, further comprising a second monomer selected from the group consisting of acrylic acids, acrylates, and acrylamides.

In certain embodiments, the present invention relates to a polymer, comprising a monomer represented by 1 and the attendant definitions, further comprising a second monomer, wherein said second monomer is acrylic acid, 2-hydroxyethyl acrylate, oligo(ethylene glycol) 2-methacrylate, acrylamide, N,N-dimethylacrylamide, or N-(tris(hyrdoxymethyl)methyl)acrylamide.

In certain embodiments, the present invention relates to a polymer, comprising a monomer represented by 2:

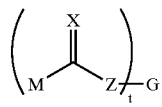

wherein

X represents independently for each occurrence O or S;

M represents independently for each occurrence —O—NH—Q;

Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO(CR$_2$)$_n$C(O)—, 2-alkylacryloylO(CR$_2$)$_n$C(O)—, 3-alkylacryloylO(CR$_2$)$_n$C(O)—, 2,3-dialkylacryloylO(CR$_2$)$_n$C(O)—, 3,3-dialkylacryloylO(CR$_2$)$_n$C(O)—, 2,3,3-trialkylacryloylO(CR$_2$)$_n$C(O)—, (diene)C(O)—, (vinyl)(CR$_2$)$_n$C(O)—, or (vinyl)ArC(O)—;

R represents independently for each occurrence H or alkyl;

Z represents —NH(CR$_2$)$_n$NH—, or —NH(CR$_2$)$_n$J(CR$_2$)$_m$NH—;

Ar represents independently for each occurrence aryl or heteroaryl;

J represents independently for each occurrence O, S, NR, cycloalkyl, heterocyclyl, (CH$_2$CH$_2$O)n, or (CH$_2$CH$_2$N(R))$_n$;

G represents (CR$_{(4-t)}$), aryl, or heteroaryl;

n represents independently for each occurrence an integer in the range 1–10;

m represents independently for each occurrence an integer in the range 0–10; and t represents 3 or 4.

In certain embodiments, the present invention relates to a polymer, comprising a monomer represented by 2 and the attendant definitions, wherein X represents O. In certain embodiments, the present invention relates to a polymer, comprising a monomer represented by 2 and the attendant definitions, wherein M represents —O—NH—Q.

In certain embodiments, the present invention relates to a polymer, comprising a monomer represented by 2 and the attendant definitions, wherein Q represents acryloyl, or 2-methacryloyl.

In certain embodiments, the present invention relates to a polymer, comprising a monomer represented by 2 and the attendant definitions, wherein R represents H.

In certain embodiments, the present invention relates to a polymer, comprising a monomer represented by 2 and the attendant definitions, wherein X represents O; and M represents —O—NH—Q.

In certain embodiments, the present invention relates to a polymer, comprising a monomer represented by 2 and the attendant definitions, wherein X represents O; M represents —O—NH—Q; and Q represents acryloyl, or 2-methacryloyl.

In certain embodiments, the present invention relates to a polymer, comprising a monomer represented by 2 and the attendant definitions, wherein X represents O; M represents —O—NH—Q; Q represents acryloyl, or 2-methacryloyl; and R represents H.

In certain embodiments, the present invention relates to a polymer, comprising a monomer represented by 2 and the attendant definitions, further comprising a second monomer selected from the group consisting of acrylic acids, acrylates, and acrylamides.

In certain embodiments, the present invention relates to a polymer, comprising a monomer represented by 2 and the attendant definitions, further comprising a second monomer, wherein said second monomer is acrylic acid, 2-hydroxyethyl acrylate, oligo(ethylene glycol) 2-methacrylate, acrylamide, N,N-dimethylacrylamide, or N-(tris(hyrdoxymethyl)methyl)acrylamide.

Gels and Hydrogels of the Invention

Hydrogels are a well recognized class of polymeric materials. These materials are characterized by their water-insolubility, hydrophilicity, high-water absorbability and swellable properties. The molecular components or units or segments of the hydrogel are characterized by a significant portion of hydrophilic components, units or segments, such as segments having ionic species or dissociable species such as acids (e.g., carboxylic acids, phosphonic acids, sulfonic acids, sulfinic acids, phosphinic acids, etc.), bases (e.g., amine groups, proton accepting groups), or other groups that develop ionic properties when immersed in water (e.g., sulfonamides). Acryloyl groups (and to a lesser degree methacryloyl groups) and the class of acrylic polymers, polymer chains containing or terminated with oxyalkylene units (such as polyoxyethylene chains or polyoxyethylene/polyoxypropylene copolymer chains) are also well recognized as hydrophilic segments that may be present within hydrophilic polymers Certain preferred water insoluble polymeric compositions useful in the present invention are listed below, although the entire class of hydrogel materials known in the art may be used to various degrees. The polymers set forth below and containing acid groups can be, as an option, partially or completely neutralized with alkali metal bases either as the monomer or the polymer or both. While the list below contains many of the preferred polymers which may be used in accordance with the present invention, the present invention is not limited to just these polymers and generally polymers traditionally understood as hydrogels by those skilled in the art can also be used: a) polyacrylic acid, polymethacrylic acid, polymaleic acid, copolymers thereof, and alkali metal and ammonium salts thereof; b) graft copolymers of starch and acrylic acid, starch and saponified acrylonitrile, starch and saponified ethyl acrylate, and acrylate-vinyl acetate copolymers saponified; c) polyvinyl alcohol, polyvinylpyrrolidone, polyvinyl alkylether, polyethylene oxide, polyacrylamide, and copolymers thereof; d) copolymers of maleic anhydride and alkyl vinylethers; and e) saponified starch graft copolymers of acrylonitrile, acrylate esters, vinyl acetate, and starch graft copolymers of acrylic acid, methylacrylic acid, and maleic acid.

The above exemplary polymers are cross-linked either during the polymerization or after the core is encapsulated. This cross-linking is achieved using the cross-linking agents of the present invention by methods known to those skilled in the art. This cross-linking can be initiated in the presence of radiation or a chemical free radical initiator.

One of the useful properties of hydrogels is their ability to absorb water and swell without dissolution of the matrix. As the hydrogel swells, the pore size of the hydrogel increases which enhances uptake of aqueous solutions and the diffusion of compounds out of the hydrogel. These properties have allowed use of hydrogels as controlled drug release systems and as absorbent materials. However, the rate of swelling of dried hydrogels upon exposure to an aqueous solution is limited by diffusion of water into the glassy polymer matrix. Conventional dried hydrogels have relatively small pore sizes resulting in slow swelling and release or absorption of liquids. The size of the pores in the hydrogel can be a factor used in the selection of hydrogels with the appropriate properties for the specific removable caps in the practice of the present invention. The larger the pore size, the generally higher rate of initial swelling a hydrogel undergoes.

Among the many hydrogel polymers which are useful as matrix polymers include poly(hydroxyalkyl methacrylate)s of which poly-(2-hydroxyethyl methacrylate), poly(glyceryl methacrylate) and poly(hydroxypropyl methacrylate) are well-known and identified in the literature as (P-HEMA), (P-GMA) and (P-(HPMA), respectively. Other hydrogel polymers include poly(acrylamide), poly(methacrylamide), poly(N-vinyl-2-pyrrolidine), and poly(vinyl alcohol), hydroxypropyl guar, high molecular weight polypropylene glycol or polyethylene glycol, and the like. It is known to produce sparingly cross-linked, water-insoluble but hydrophilic polymers which can be used as carriers for biologically active, at least slightly water-soluble substances by copolymerization of a major amount of hydrophilic mono-olefinic monomers and a minor amount ranging between 0.01 and 15% of said mono-olefinic monomers, of a low molecular weight cross-linker. As mono-olefinic monomers, particularly monoesters of acrylic or methacrylic acid with polyfunctional alcohols, such as ethyleneglycol monomethacrylate, and as cross-linking agents particularly diesters of said acids with said alcohols, such as ethyleneglycol bis-methacrylate are used and the copolymerization is carried out in the presence of water, see U.S. Pat. No. 3,220,960 or a water-free system, see U.S. Pat. No. 3,520, 949. Low molecular as well as macromolecular, water-soluble substances, such as polyethyleneoxide monomethacrylate together with a minor amount of the corresponding bis-methacrylate have been used (see U.S. Pat. No. 3,220,960) as monomers and cross-linking agents. The water-insoluble, but hydrophilic copolymers and the process for their production have been modified in several directions and adapted to specific purposes, e.g. the production of soft contact lenses, U.S. Pat. No. 3,220,960 and Reissue No. 27,401, and the copolymerization in the presence of linear polyamide resin in order to improve or modify the mechanical properties of shaped bodies formed from the obtained polymers, U.S. Pat. No. 3,520,949.

Non-limiting examples of the unsaturated monomers used as a starting material include those polymerizable monomers known to be soluble in water. Examples of these unsaturated monomer are: monomers containing an acid group, such as acrylic acid, beta-acryloyloxypropionic acid, methacrylic acid, crotonic acid, maleic acid, maleic anhydride, fumaric acid, itaconic acid, cinnamic acid, sorbic acid, 2-(meth) acryloylethane sulfonic acid, 2-(meth)acryloylpropane sulfonic acid, 2-(meth)acrylamido-2-methylpropane sulfonic acid, vinyl sulfonic acid, styrene sulfonic acid, allyl sulfonic acid, vinyl phosphonic acid and 2-(meth)acryloyloxyethyl phosphate, and alkaline metal salts and alkaline earth metal salts, ammonium salts, and alkyl amine salts thereof, dialkyl amino alkyl(meth)acrylates, such as N,N-dimethylaminoethyl(meth)acrylate and N,N-dimethylaminopropyl(meth)acrylate, and quaternary compounds thereof (for example, a reaction product produced with alkylhalide, and a reaction product produced with dialkyl sulfuric acid); dialkyl amino hydroxyalkyl(meth) acrylates, and quaternary compounds thereof; N-alkyl vinyl pyridine halide; hydroxyalkyl(meth)acrylates, such as hydroxymethyl (meth)acrylate, 2-hydroxyethyl(meth) acrylate, and 2-hydroxypropyl (meth)acrylate; acrylamide, methacrylamide, N-ethyl (meth)acrylamide, N-propyl (meth)acrylamide, N-isopropyl(meth)acrylamide, N,N-dimethyl (meth)acrylamide, 2-hydroxyethyl (meth)acrylate, 2-hydroxypropyl (meth)acrylate, methoxypolyethylene glycol (meth)acrylate, polyethylene glycol mono(meth) acrylate, vinylpyridine, N-vinylpyrrolidone, N-acryloyl piperidine, and N-acryloyl pyrrolidine; vinyl acetate; and alkyl (meth)acrylates, such as methyl (meth)acrylate, and ethyl (meth)acrylate. These monomers may be used individually, or in combination.

In certain embodiments, the present invention relates to a crosslinked gel, comprising a hydrophobic polymer; and a compound represented by 1 or 2 and any of their respective attendant definitions.

In certain embodiments, the present invention relates to a crosslinked gel as defined above, wherein said hydrophobic polymer comprises an alkyl acrylate, alkyl alkylacrylate, alkyl acrylamide, or alkyl alkylacrylamide.

In certain embodiments, the present invention relates to a crosslinked gel as defined above, wherein said hydrophobic polymer comprises an alkyl methacrylate.

In certain embodiments, the present invention relates to a crosslinked gel as defined above, wherein said hydrophobic polymer comprises methyl methacrylate, ethyl methacrylate, n-butyl methacrylate, or tert-butyl methacrylate.

In certain embodiments, the present invention relates to a crosslinked hydrogel, comprising a hydrophilic polymer; and a compound represented by 1 or 2 and any of their respective attendant definitions.

In certain embodiments, the present invention relates to a crosslinked hydrogel as defined above, wherein said hydrophilic polymer comprises an acrylic acid, acrylate, or acrylamide.

In certain embodiments, the present invention relates to a crosslinked hydrogel as defined above, wherein said hydrophilic polymer comprises acrylic acid, 2-hydroxyethyl acrylate, oligo(ethylene glycol) 2-methacrylate, acrylamide, N,N-dimethylacrylamide, or N-(tris(hydroxymethyl) methyl)acrylamide.

In certain embodiments, the present invention relates to a crosslinked hydrogel as defined above, wherein said hydrophilic polymer consists of a first acrylamide and a second acrylamide.

In certain embodiments, the present invention relates to a crosslinked hydrogel as defined above, wherein said first acrylamide is acrylamide or N,N-dimethylacrylamide.

In certain embodiments, the present invention relates to a crosslinked hydrogel as defined above, wherein said second acrylamide is N-(tris(hydroxymethyl)methyl)acrylamide.

In certain embodiments, the present invention relates to a crosslinked hydrogel as defined above, wherein said first acrylamide is acrylamide or N,N-dimethylacrylamide; and said second acrylamide is N-(tris(hydroxymethyl)methyl) acrylamide.

In certain embodiments, the present invention relates to a crosslinked hydrogel as defined above, wherein said hydrophilic polymer consists of an acrylamide and an acrylate.

In certain embodiments, the present invention relates to a crosslinked hydrogel as defined above, wherein said acrylamide is acrylamide or N,N-dimethylacrylamide.

In certain embodiments, the present invention relates to a crosslinked hydrogel as defined above, wherein said acrylate is acrylic acid, 2-hydroxyethyl acrylate, or oligo(ethylene glycol) 2-methacrylate.

In certain embodiments, the present invention relates to a crosslinked hydrogel as defined above, wherein said acrylamide is acrylamide or N,N-dimethylacrylamide; and said acrylate is acrylic acid, 2-hydroxyethyl acrylate, or oligo (ethylene glycol) 2-methacrylate.

In certain embodiments, the present invention relates to a crosslinked hydrogel as defined above, wherein said hydrophilic polymer consists of a first acrylate and a second acrylate.

In certain embodiments, the present invention relates to a crosslinked hydrogel as defined above, wherein said first acrylate is acrylic acid, 2-hydroxyethyl acrylate, or oligo (ethylene glycol) 2-methacrylate.

In certain embodiments, the present invention relates to a crosslinked hydrogel as defined above, wherein said first acrylate is acrylic acid, 2-hydroxyethyl acrylate, or oligo (ethylene glycol) 2-methacrylate; and said second acrylate is acrylic acid, 2-hydroxyethyl acrylate, or oligo(ethylene glycol) 2-methacrylate.

Methods of the Invention

The polymerization methods of the present invention may be practiced in water, organic solvents, or a mixture of both. The concentration of the unsaturated monomer in the solution (hereinafter referred to as the monomer solution) is exemplified in a non-limiting manner within this description as preferably but not exclusively including a range of from 20 weight percent to 65 weight percent, more preferably from 25 weight percent to 60 weight percent, most preferably from 30 weight percent to 45 weight percent.

As noted above, it is also possible to use water and an organic solvent soluble in water together as a solvent for the monomer solution. Examples of suitable organic solvents are methyl alcohol, ethyl alcohol, acetone, dimethyl sulfoxide, ethylene glycol monomethyl ether, glycerin, (poly)ethylene glycol, (poly)propylene glycol, and alkylene carbonate. These organic solvents may be used individually, or in combination.

Finally, also as noted above, a pure organic solvent may be used for the monomer solution.

The polymerization method is not particularly limited, and various methods can be used. Examples include radical polymerization using a radical polymerization initiator, irradiation-induced polymerization, electron radiation-induced polymerization, and ultraviolet-induced polymerization using a photosensitizer. Among these methods, radical polymerization is preferred.

As for the radical polymerization step, there are various polymerization methods, such as aqueous solution polymerization, cast polymerization which is performed within a mold, thin-layer polymerization which is performed on a belt conveyer, polymerization which is performed while making generated hydrogel polymer into small pieces, reversed-phase suspension polymerization, reversed-phase emulsion polymerization, precipitation polymerization, and bulk polymerization. Among these polymerization methods, the aqueous solution polymerization which polymerizes the unsaturated monomer in the form of aqueous solution is more preferred because the polymerization temperature can be easily controlled. The aqueous solution polymerization of the unsaturated monomer may be performed either continuously or batch-wise, or may be performed under suction, pressure, or atmospheric pressure. Generally, it is preferred to dissolve or disperse a radical polymerization initiator in an monomer solution in advance. Examples of the radical polymerization initiator include: peroxides, such as ammonium persulfate, potassium persulfate, sodium persulfate, hydrogen peroxide, benzoyl peroxide, cumene hydroperoxide, and di-t-butyl peroxide; redox initiators formed by combining the above-mentioned peroxides and reducing agents, such as sulfite, bisulfite, thiosulfate, formamidine sulfinic acid, and ascorbic acid; acrylic acid salts of azo-compound containing an amino group represented by general formula (1) or (2) above; and azo polymerization initiators, such as hydrochlorides of the azo-compound containing an amino group. These radical polymerization initiators may be used individually, or in combination. The amount of the radical polymerization initiator with respect to the unsaturated monomer is varied depending on the combination of the unsaturated monomer and the radical polymerization initiator. However, the amount of the radical polymerization initiator to be used is within a range of preferably from 0.0005 weight parts to 5 weight parts, more preferably from 0.005 weight parts to 2.5 weight parts, based on 100 parts by weight of the unsaturated monomer. If the amount of the radical polymerization initiator is less than 0.0005 weight parts, the amount of unreacted unsaturated monomers increases, causing an unfavorable increase of the residual monomer content in the resulting water-absorbent resin. Although the temperature at the initiation of polymerization varies depending on the type of a radical polymerization initiator used, it is preferably within a range of from 30° C. to 120° C., more preferably from 40° C. to 80° C.

In certain embodiments, the present invention relates to a method of preparing a polymer comprising a monomer represented by 1 and the attendant definitions, comprising reacting a monomer represented by 1 and the attendant definitions with a second monomer in the presence of an initiator.

In certain embodiments, the present invention relates to a method of preparing a polymer comprising a monomer represented by 2 and the attendant definitions, comprising reacting a monomer represented by 2 and the attendant definitions with a second monomer in the presence of an initiator.

In certain embodiments, the present invention relates to a method of preparing a crosslinked gel comprising a monomer represented by 1 or 2 and the attendant definitions, comprising reacting a monomer represented by 1 or 2 and the attendant definitions with a hydrophobic monomer in the presence of an initiator.

In certain embodiments, the present invention relates to a method of preparing a crosslinked gel comprising a monomer represented by 1 or 2 and the attendant definitions, comprising reacting a monomer represented by 1 or 2 and the attendant definitions with a hydrophilic monomer in the presence of an initiator.

EXEMPLIFICATION

The invention now being generally described, it will be more readily understood by reference to the following examples, which are included merely for purposes of illustration of certain aspects and embodiments of the present invention, and are not intended to limit the invention.

Example 1

Synthesis of N-methacryloylhydroxylamine (MHA)

MHA was synthesized by reacting methyl methacrylate (MMA) with hydroxylamine in a basic aqueous solution. In a 700 mL beaker, hydroxylamine hydrochloride (70 g) was added, which was dissolved in 150 g of sterile water. The aqueous solution thus obtained was cooled to 0° C., to which MMA (100 g) was added. In another beaker, sodium hydroxide (80 g) was dissolved in sterile water (140 g). After cooling to 0° C., this basic aqueous solution was dropwise added to the first beaker with vigorous stirring. At this stage, the formation of MHA was confirmed by testing the reaction mixture with an acidic aqueous solution of ferric chloride (The deep-red color of the complex formed between MHA and $FeCl_3$ appeared instantaneously). After the reaction lasted 3 h at 0° C., the system was concentrated by distillation under reduced pressure and the residue was extracted with ether (200 mL) for six times. The ether phase was concentrated by evaporation and a solid product was obtained by crystallization from a mixture of ether and hexane. The 1H NMR spectrum of this crystal is consistent with the molecular structure of MHA (in DMSO-$D_6$: —NHOH, 10.70 and 8.79 ppm; C=$CH_2$, 5.28 and 5.57 ppm; —$CH_3$, 1.82 ppm) and no impurity was detected.

Example 2

Synthesis of a Crosslinker: MHA-DIH

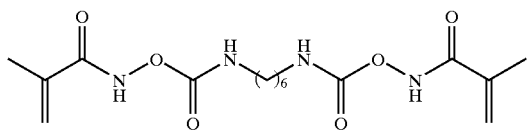

MHA-DIH is the adduct of one 1,6-diisocyanatohexane (DIH) molecule and two MHA molecules, which was prepared by reacting DIH with MHA in THF at room temperature. A well-dried 250 mL round-bottom flask containing a magnetic stirring bar was protected with nitrogen, to which MHA (11.1 g, 0.11 mol) was first added and this was followed by the addition of $CaH_2$-dried THF (40 g). After MHA dissolved completely, DIH (8.3 mL, 0.05 mol) was diluted with THF (16 g) and dropwise added with a dried syringe over 15 min. The reaction was allowed to last 24 h at room temperature with stirring. Then, the reaction system was concentrated by evaporating and put into the refrigerator for crystallization. The white crystal crosslinker MHA-DIH was obtained by filtration, washed with THF three times, and vacuum-dried overnight (Yield=46% based on the feed amount of DIH). Its very high purity was conformed by 1H NMR measurement (in DMF-$d_7$): 11.47 ppm, 2H, O=C—NHO; 7.58 ppm, 2H, O=C—NH—C; 5.47 and 5.80 ppm, 4H, $CH_2$=; 3.14 ppm, 4H, —$NHCH_2CH_2CH_2CH_2CH_2CH_2NH$—; 1.92 ppm, 6H, —$CH_3$; 1.50 ppm, 4H, —$NHCH_2CH_2CH_2CH_2CH_2CH_2NH$—; 1.33 ppm, 4H, $NHCH_2CH_2CH_2CH_2CH_2CH_2NH$—.

Example 3

Synthesis of a Crosslinker: MHA-DIB

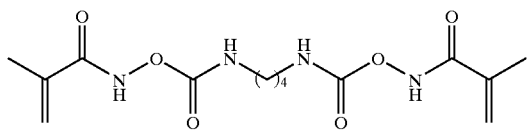

MHA-DIB is the adduct of one 1,4-diisocyanatobutane (DIB) molecule and two MHA molecules, which was prepared by reacting DIB with MHA in THF at room temperature. As described for the preparation of MHA-DIH, a similar synthetic procedure was also applied to MHA-DIB. A white crystal product was obtained with a yield of 39% based on the feed amount of DIB. Similar to that of MHA-DIH, its NMR spectrum is completely consistent with its molecular structure (in DMF-$d_7$): 11.48 ppm, 2H, O=C—NHO; 7.60 ppm, 2H, O=C—NH—C; 5.48 and 5.81 ppm, 4H, $CH_2$=; 3.16 ppm, 4H, $NHCH_2CH_2CH_2CH_2NH$; 1.93 ppm, 6H, —$CH_3$; 1.55 ppm, 4H, —$NHCH_2CH_2CH_2CH_2NH$—.

Example 4

Preparation of DMA Homopolymer Beads Using MHA-DIH as the Crosslinker

A 500 mL open-mouth jacketed flask was equipped with a mixer, a thermometer and a temperature controller, to which 150 mL of mineral oil and 0.12 g of sorbitan sesquioleate (SSO) were sequentially added. This system was heated to 60° C. by circulating water with stirring (350 rpm), and used as the continuing oil phase.

Simultaneously, the water phase was prepared in a small beaker as follows. Sodium chloride (23.2 g) and sodium acetate (11.0 g) were first dissolved in distilled water (81.6 mL). Then, this aqueous solution was mixed with glycerol (163 mL) with magnetic stirring. Finally, the pH value of this mixture was regulated to 6.0 by adding acetic acid.

The buffer solution (pH=6.25 mL) was used to dissolve DMA (5.0 g). To this solution, the crosslinker MHA-DIH (25 w % DMF solution, 1.8 g) was dropwise added with stirring. This mixture was heated to 60° C. in an oil bath. As soon as the initiator APS (0.15 g) was added, this water phase was transferred into the oil phase with fast stirring (650 rpm), and TMEDA (0.4 mL) was added immediately to accelerate the reaction. After the polymerization lasted 30 min, the mixture was rinsed into about 120 mL of water (pH=3.0) to separate the beads. The beads in water phase were washed with water (pH=3) for more than five times, then, immersed in a buffer (pH=2) and stored in the refrigerator (4° C.). This kind of beads in the buffer solution (pH=7.4) degraded completely within 5 days at 37° C. As shown in Table 1, by using different monomers and/or crosslinker, several kinds of homopolymer beads were prepared.

TABLE 1

| Preparation of homo- and co-polymer beads. | | | | |
|---|---|---|---|---|
| Monomer 1 (%)[a] | Monomer 2 (%)[a] | Crosslinker (%)[b] | Degradation time at pH = 7.4[c] | Degradation time at pH = 2[d] |
| DMA 100 | | MHA-DIH 9 | 5 days | No degradation after 2 months |
| TS 100 | | MHA-DIH 9 | 1.5 days | No degradation after 2 months |
| HEA 100 | | MHA-DIH 9 | >16 days | No degradation after 2 months |

TABLE 1-continued

Preparation of homo- and co-polymer beads.

| Monomer 1 (%)[a] | Monomer 2 (%)[a] | Crosslinker (%)[b] | Degradation time at pH = 7.4[c] | Degradation time at pH = 2[d] |
|---|---|---|---|---|
| DMA 80 | TS 20 | MHA-DIH 9 | 3 days | No degradation after 2 months |
| DMA 50 | TS 50 | MHA-DIH 9 | 1.5 days | No degradation after 2 months |
| DMA 80 | HEA 20 | MHA-DIH 9 | 3.5 days | No degradation after 2 months |
| DMA 50 | HEA 50 | MHA-DIH 9 | 7 days | No degradation after 2 months |
| DMA 100 | | MHA-DIB 9 | 2.5 days | No degradation after 2 months |
| TS 100 | | MHA-DIB 9 | 1 day | No degradation after 2 months |
| HEA 100 | | MHA-DIB 9 | >5 days | No degradation after 2 months |
| DMA 80 | TS 20 | MHA-DIB 9 | 1.5 days | No degradation after 2 months |
| DMA 50 | TS 50 | MHA-DIB 9 | 2.5 days | No degradation after 2 months |
| DMA 50 | HEA 50 | MHA-DIB 9 | 3 days | No degradation after 2 months |

[a]TS: [tris(hydroxymethyl)]methyl acrylate; HEA: 2-hydroxyethl methacrylate; DMA: N,N-dimethylacrylamide.
[b]Compared to the total amount of the monomer(s), 9 wt % of the crosslinker was used.
[c]At 37 C.
[d]At 5 C.

Example 5

Preparation of DMA-TS Copolymer Beads

The oil phase preparation was carried out in the same way as used in Example 5. However, instead of only one monomer, both TS and DMA were included in the water phase. 1.0 g of TS was first dissolved in the buffer solution (25 g, pH=6; see Example 5) at 45° C. Then, 4.0 g of DMA and a DMF solution of the crosslinker MHA-DIB (25 wt %, 1.8 g) were dropwise added with stirring. This system was heated to 60° C. in an oil bath. Upon the addition of 0.15 g of APS, this mixture was poured into the oil phase and the accelerator TMEDA (0.40 mL dissolved in 2 mL mineral oil) was added immediately. About 30 min later, the beads thus obtained were purified in the way similar to that used in Example 5. This kind of beads in the buffer solution (pH= 7.4) degraded completely within 1.5 days at 37° C. As shown in Table 1, by using different monomers and/or crosslinker, several kinds of copolymer beads were prepared.

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:
1. A compound represented by 1:

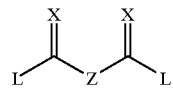

wherein
X represents independently for each occurrence O or S;
L represents independently for each occurrence —O—NH—Q;
Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO $(CR_2)_nC(O)$—, 2-alkylacryloylO$(CR_2)_nC(O)$—, 3-alkylacryloylO$(CR_2)_nC(O)$—, 2,3-dialkylacryloylO$(CR_2)_nC(O)$—, 3,3-dialkylacryloylO$(CR_2)_nC(O)$—, 2,3,3-trialkylacryloylO$(CR_2)_nC(O)$—, (diene)C(O)—, (vinyl)$(CR_2)_nC(O)$—, or (vinyl)ArC(O)—;
R represents independently for each occurrence H or alkyl;
Z represents —NH$(CR_2)_n$NH—, or —NH$(CR_2)_n$J$(CR_2)_m$NH—;
Ar represents independently for each occurrence aryl or heteroaryl;
J represents independently for each occurrence O, S, NR, cycloalkyl, heterocyclyl, $(CH_2CH_2O)_n$, or $(CH_2CH_2N(R))_n$;
n represents independently for each occurrence an integer in the range 1–10; and
m represents independently for each occurrence an integer in the range 0–10.
2. The compound of claim 1, wherein X represents O.
3. The compound of claim 1, wherein Q represents acryloyl, or 2-methacryloyl.

4. The compound of claim 1, wherein R represents H.

5. The compound of claim 1, wherein Z represents —NH(CR$_2$)$_n$NH—.

6. The compound of claim 1, wherein X represents O; and L represents —O—NH—Q.

7. The compound of claim 1, wherein X represents O; L represents —O—NH—Q; and Q represents acryloyl, or 2-methacryloyl.

8. The compound of claim 1, wherein X represents O; L represents —O—NH—Q; Q represents acryloyl, or 2-methacryloyl; and R represents H.

9. The compound of claim 1, wherein X represents O; L represents —O—NH—Q; Q represents acryloyl, or 2-methacryloyl; R represents H; and Z represents —NH(CR$_2$)$_n$NH—.

10. A compound represented by 2:

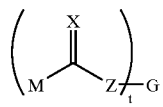

wherein

X represents independently for each occurrence O or S;

M represents independently for each occurrence —O—NH—Q;

Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO(CR$_2$)$_n$C(O)—, 2-alkylacryloylO(CR$_2$)$_n$C(O)—, 3-alkylacryloylO(CR$_2$)$_n$C(O)—, 2,3-dialkylacryloylO(CR$_2$)$_n$C(O)—, 3,3-dialkylacryloylO(CR$_2$)$_n$C(O)—, 2,3,3-trialkylacryloylO(CR$_2$)$_n$C(O)—, (diene)C(O)—, (vinyl)(CR$_2$)$_n$C(O)—, or (vinyl)ArC(O)—;

R represents independently for each occurrence H or alkyl;

Z represents —NH(CR$_2$)$_n$NH—, or —NH(CR$_2$)$_n$J(CR$_2$)$_m$NH—;

Ar represents independently for each occurrence aryl or heteroaryl;

J represents independently for each occurrence O, S, NR, cycloalkyl, heterocyclyl, (CH$_2$CH$_2$O)$_n$, or (CH$_2$CH$_2$N(R))$_n$;

G represents (CR$_{(4-t)}$), aryl, or heteroaryl;

n represents independently for each occurrence an integer in the range 1–10;

m represents independently for each occurrence an integer in the range 0–10; and t represents 3 or 4.

11. The compound of claim 10, wherein X represents O.

12. The compound of claim 10, wherein Q represents acryloyl, or 2-methacryloyl.

13. The compound of claim 10, wherein R represents H.

14. The compound of claim 10, wherein X represents O; and M represents —O—NH—Q.

15. The compound of claim 10, wherein X represents O; M represents —O—NH—Q; and Q represents acryloyl, or 2-methacryloyl.

16. The compound of claim 10, wherein X represents O; M represents —O—NH—Q; Q represents acryloyl, or 2-methacryloyl; and R represents H.

17. A method of preparing a compound represented by 1:

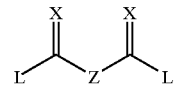

wherein

X represents independently for each occurrence O or S;

L represents independently for each occurrence —O—NH—Q;

Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO(CR$_2$)$_n$C(O)—, 2-alkylacryloylO(CR$_2$)$_n$C(O)—, 3-alkylacryloylO(CR$_2$)$_n$C(O)—, 2,3-dialkylacryloylO(CR$_2$)$_N$C(O)—, 3,3-dialkylacryloylO(CR$_2$)$_n$C(O)—, 2,3,3-trialkylacryloylO(CR$_2$)$_n$C(O)—, (diene)C(O)—, (vinyl)(CR$_2$)$_n$C(O)—, or (vinyl)ArC(O)—;

R represents independently for each occurrence H or alkyl;

Z represents —NH(CR$_2$)$_n$NH—, or —NH(CR$_2$)$_n$J(CR$_2$)$_m$NH—;

Ar represents independently for each occurrence aryl or heteroaryl;

J represents independently for each occurrence O, S, NR, cycloalkyl, heterocyclyl, (CH$_2$CH$_2$O)$_n$, or (CH$_2$CH$_2$N(R))$_n$;

n represents independently for each occurrence an integer in the range 1–10; and m represents independently for each occurrence an integer in the range 0–10.

(a) reacting a hydroxylamine with an acrylate, thereby forming an acrylic hydroxamic acid; and (b) reacting said acrylic hydroxamic acid with a diisocyanate.

18. A method of preparing a compound represented by 2:

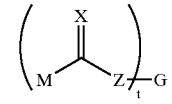

wherein

X represents independently for each occurrence O or S;

M represents independently for each occurrence —O—NH—Q;

Q represents independently for each occurrence acryloyl, 2-alkylacryloyl, 3-alkylacryloyl, 2,3-dialkylacryloyl, 3,3-dialkylacryloyl, 2,3,3-trialkylacryloyl, acryloylO(CR$_2$)$_n$C(O)—, 2-alkylacryloylO(CR$_2$)$_n$C(O)—, 3-alkylacryloylO(CR$_2$)$_n$C(O)—, 2,3-dialkylacryloylO(CR$_2$)$_n$C(O)—, 3,3-dialkylacryloylO(CR$_2$)$_n$C(O)—, 2,3,3-trialkylacryloylO(CR$_2$)$_n$C(O)—, (diene)C(O)—, (vinyl)(CR$_2$)$_n$C(O)—, or (vinyl)ArC(O)—;

R represents independently for each occurrence H or alkyl;

Z represents —NH(CR$_2$)$_n$NH—, or —NH(CR$_2$)$_n$J(CR$_2$)$_m$NH—;

Ar represents independently for each occurrence aryl or heteroaryl;

J represents independently for each occurrence O, S, NR, cycloalkyl, heterocyclyl, $(CH_2CH_2O)_n$, or $(CH_2CH_2N(R))_n$;

G represents $(CR_{(4-t)})$, aryl, or heteroaryl;

n represents independently for each occurrence an integer in the range 1–10;

m represents independently for each occurrence an integer in the range 0–10; and t represents 3 or 4;

comprising:

(a) reacting a hydroxylamine with an acrylate, thereby forming a hydroxamic acid; and (b) reacting said hydroxamic acid with a triisocyanate or tetraisocyanate.

* * * * *